(12) United States Patent
Reed et al.

(10) Patent No.: US 11,131,670 B2
(45) Date of Patent: Sep. 28, 2021

(54) IMMUNOASSAY TEST DEVICE WITH TWO FLUID FLOW PATHS FOR DETECTION AND DIFFERENTIATION OF TWO OR MORE ANALYTES

(71) Applicant: Quidel Corporation, San Diego, CA (US)

(72) Inventors: Robert Reed, Carlsbad, CA (US); Irene Sinn, San Diego, CA (US); Robert Weiller, Encinitas, CA (US); Jason McClure, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 962 days.

(21) Appl. No.: 15/247,633

(22) Filed: Aug. 25, 2016

(65) Prior Publication Data

US 2017/0059566 A1 Mar. 2, 2017

Related U.S. Application Data

(60) Provisional application No. 62/210,880, filed on Aug. 27, 2015, provisional application No. 62/268,455, filed on Dec. 16, 2015, provisional application No. 62/271,101, filed on Dec. 22, 2015.

(51) Int. Cl.
| | | |
|---|---|---|
| *G01N 33/569* | (2006.01) | |
| *G01N 33/558* | (2006.01) | |

(52) U.S. Cl.
CPC ..... *G01N 33/56911* (2013.01); *G01N 33/558* (2013.01); *G01N 2333/20* (2013.01); *G01N 2469/20* (2013.01); *G01N 2800/56* (2013.01); *Y02A 50/30* (2018.01)

(58) Field of Classification Search
CPC ........... G01N 33/56911; G01N 33/558; G01N 2333/20; G01N 2469/20; G01N 2800/56; Y02A 50/30
USPC ...................................................... 435/70.1
See application file for complete search history.

(56) References Cited

U.S. PATENT DOCUMENTS

| | | | | |
|---|---|---|---|---|
| 5,643,733 A | * | 7/1997 | Robinson | C07K 14/20 435/7.1 |
| 5,643,751 A | | 7/1997 | Robinson et al. | |
| 6,475,492 B1 | | 11/2002 | Philipp et al. | |
| 6,528,321 B1 | * | 3/2003 | Fitzgerald | G01N 30/90 422/408 |
| 6,528,323 B1 | | 3/2003 | Thayer et al. | |
| 6,660,274 B2 | | 12/2003 | Philipp | |
| 6,689,317 B1 | | 2/2004 | Rees | |
| 6,716,574 B2 | | 4/2004 | Mathiesen et al. | |
| 6,719,983 B2 | | 4/2004 | Norris et al. | |
| 7,109,023 B2 | | 9/2006 | Kang et al. | |
| 7,189,522 B2 | | 3/2007 | Esfandiari | |
| 7,229,839 B2 | | 6/2007 | Thayer et al. | |
| 7,887,815 B2 | | 2/2011 | Dattwyler et al. | |
| 8,071,109 B2 | | 12/2011 | Norris et al. | |
| 8,338,556 B1 | | 12/2012 | Dougherty | |
| 8,354,240 B2 | | 1/2013 | Norris et al. | |
| 2001/0023076 A1 | * | 9/2001 | Guan | G01N 33/558 436/514 |
| 2006/0019406 A1 | * | 1/2006 | Wei | G01N 33/558 436/514 |
| 2010/0173423 A1 | * | 7/2010 | Zuaretz | G01N 33/54386 436/164 |
| 2012/0142023 A1 | * | 6/2012 | Ascoli | G01N 33/56911 435/7.5 |
| 2013/0130404 A1 | | 5/2013 | Rajesh et al. | |
| 2013/0230844 A1 | * | 9/2013 | Egan | G01N 21/6486 435/5 |
| 2015/0017666 A1 | | 1/2015 | Dattwyler et al. | |
| 2015/0253320 A1 | * | 9/2015 | Kamei | G01N 33/54366 435/5 |
| 2015/0285795 A1 | | 10/2015 | Esfandiari | |
| 2016/0258943 A1 | * | 9/2016 | Esfandiari | G01N 33/54366 |

(Continued)

FOREIGN PATENT DOCUMENTS

| | | |
|---|---|---|
| CN | 203337669 U | 12/2013 |
| CN | 104374912 A | 2/2015 |
| CN | 204241484 U | 4/2015 |

(Continued)

OTHER PUBLICATIONS

International Search Report from PCT Patent Application No. PCT/US2016/048763, 8 pages, dated Nov. 8, 2016.

(Continued)

*Primary Examiner* — Ann Y Lam
(74) *Attorney, Agent, or Firm* — McDermott Will & Emery LLP; Judy M. Mohr; Brett A. Schweers

(57) ABSTRACT

A device for determining presence or absence of infection due to an infectious agent is described. The device comprises a sample receiving zone configured to receive a liquid sample from a subject suspected of having an infection due to an infectious agent, the sample receiving zone positioned to distribute the sample along a first fluid flow path to a first label zone and along a second fluid flow path to a second label zone. Test lines in each fluid flow path capture a mobile detectable species as an indicator of presence or absence of the infectious agent. The device also comprises a reference line positioned in the one of the fluid flow paths. The bidirectional fluid flow paths emanate from a common sample zone and provide an efficient approach to detection and differentiate two species as indicators of the same infectious agent or as indicators of two different infectious agents.

14 Claims, 2 Drawing Sheets

Specification includes a Sequence Listing.

(56) References Cited

U.S. PATENT DOCUMENTS

2017/0082638 A1\* 3/2017 Barnum ............ G01N 33/6893

FOREIGN PATENT DOCUMENTS

| DE | 202004007021 U1 | 7/2004 | | |
|---|---|---|---|---|
| EP | 0973034 A1 | 1/2000 | | |
| JP | 2011-069800 A | 4/2011 | | |
| JP | 2014-528067 A | 10/2014 | | |
| WO | WO 1991/015769 A1 | 10/1991 | | |
| WO | WO 1995/016208 A1 | 6/1995 | | |
| WO | WO 2011/063003 A2 | 5/2011 | | |
| WO | WO 2012/078260 A1 | 6/2012 | | |
| WO | WO 2013/067524 A1 | 5/2013 | | |
| WO | WO 2014168580 | \* | 2/2014 | ........... G01N 33/558 |
| WO | WO 2014/168580 A1 | 10/2014 | | |

OTHER PUBLICATIONS

Nadala et al., "Development of a Non-O157:H7 Enterohemorrhagic *Escherichia coli* (EHEC) Lateral Flow Device", IEH Laboratories & Consulting Group, 9 pages, (2014), Online article retrieved from the internet: http://www.iehinc.com/development-of-a-non-o157h7-enterohemorrhagic-escherichia-coli-ehec-lateral-flow-device-2/.
Stefan, "Viro-Blot Anti-Borrelia-IgG/-IgM Instruction for use", Viro-Immun. Labor-Diagnostika GmbH, 3 pages, (2009), Online article retrieved from the internet: http://www.alphadia.be/files/Instruction-for-use-VIRO-BLOT-Borrelia-E.pdf.

\* cited by examiner

SEQUENCE LISTING

```
<160> NUMBER OF SEQ ID NOS: 21

<210> SEQ ID NO 1
<211> LENGTH: 17
<212> TYPE: PRT
<213> ORGANISM: Borreliella burgdorferi

<400> SEQUENCE: 1

Met Lys Lys Asn Asp Gln Ile Val Ala Ala Ile Ala Leu Arg Gly Val
1               5                   10                  15

Ala

<210> SEQ ID NO 2
<211> LENGTH: 26
<212> TYPE: PRT
<213> ORGANISM: Borreliella burgdorferi

<400> SEQUENCE: 2

Cys Met Lys Lys Asp Asp Gln Ile Ala Ala Ala Met Val Leu Arg Gly
1               5                   10                  15

Met Ala Lys Asp Gly Gln Phe Ala Leu Lys
```

```
<210> SEQ ID NO 3
<211> LENGTH: 17
<212> TYPE: PRT
<213> ORGANISM: Borreliella burgdorferi

<400> SEQUENCE: 3

Met Lys Lys Asn Asp Gln Ile Gly Ala Ala Ile Ala Leu Arg Gly Val
1               5                   10                  15

Ala

<210> SEQ ID NO 4
<211> LENGTH: 17
<212> TYPE: PRT
<213> ORGANISM: Borreliella burgdorferi

<400> SEQUENCE: 4

Met Lys Lys Asp Asp Gln Ile Ala Ala Ala Ile Ala Leu Arg Gly Met
1               5                   10                  15

Ala

<210> SEQ ID NO 5
<211> LENGTH: 26
<212> TYPE: PRT
<213> ORGANISM: Borreliella burgdorferi

<400> SEQUENCE: 5

Met Lys Lys Asp Asp Gln Ile Ala Ala Ala Met Val Leu Arg Gly Met
1               5                   10                  15

Ala Lys Asp Gly Gln Phe Ala Leu Lys Asp
            20                  25

<210> SEQ ID NO 6
<211> LENGTH: 26
<212> TYPE: PRT
<213> ORGANISM: Borreliella burgdorferi

<400> SEQUENCE: 6

Met Lys Lys Asp Asp Gln Ile Ala Ala Ala Ile Ala Leu Arg Gly Met
1               5                   10                  15

Ala Lys Asp Gly Lys Phe Ala Val Lys Asp
            20                  25

<210> SEQ ID NO 7
<211> LENGTH: 13
<212> TYPE: PRT
<213> ORGANISM: Borreliella burgdorferi

<400> SEQUENCE: 7

Val Gln Glu Gly Val Gln Gln Glu Gly Ala Gln Gln Pro
1               5                   10

<210> SEQ ID NO 8
<211> LENGTH: 10
<212> TYPE: PRT
<213> ORGANISM: Borreliella burgdorferi

<400> SEQUENCE: 8

Pro Val Val Ala Glu Ser Pro Lys Lys Pro
1               5                   10
```

<210> SEQ ID NO 9
<211> LENGTH: 11
<212> TYPE: PRT
<213> ORGANISM: Borreliella burgdorferi

<400> SEQUENCE: 9

Cys Pro Val Val Ala Glu Ser Pro Lys Lys Pro
1               5                   10

<210> SEQ ID NO 10
<211> LENGTH: 12
<212> TYPE: PRT
<213> ORGANISM: Borreliella burgdorferi

<400> SEQUENCE: 10

Leu Cys Pro Val Val Ala Glu Ser Pro Lys Lys Pro
1               5                   10

<210> SEQ ID NO 11
<211> LENGTH: 35
<212> TYPE: PRT
<213> ORGANISM: Borreliella burgdorferi

<400> SEQUENCE: 11

Tyr Gly Gln Asn Trp Thr Asn Pro Glu Asn Met Val Thr Ser Gly Pro
1               5                   10                  15

Phe Lys Leu Lys Glu Arg Ile Pro Asn Glu Lys Ile Val Phe Glu Lys
            20                  25                  30

Asn Asn Lys
        35

<210> SEQ ID NO 12
<211> LENGTH: 20
<212> TYPE: PRT
<213> ORGANISM: Borreliella burgdorferi

<400> SEQUENCE: 12

Met Thr Leu Phe Leu Phe Ile Ser Cys Asn Asn Ser Gly Lys Asp Gly
1               5                   10                  15

Asn Thr Ser Ala
        20

<210> SEQ ID NO 13
<211> LENGTH: 21
<212> TYPE: PRT
<213> ORGANISM: Borreliella burgdorferi

<400> SEQUENCE: 13

Lys Met Thr Leu Phe Leu Phe Ile Ser Cys Asn Asn Ser Gly Lys Asp
1               5                   10                  15

Gly Asn Thr Ser Ala
        20

<210> SEQ ID NO 14
<211> LENGTH: 15
<212> TYPE: PRT
<213> ORGANISM: Borreliella burgdorferi

<400> SEQUENCE: 14

Thr Ile Leu Val Asn Leu Leu Ile Ser Cys Gly Leu Thr Gly Ala
1               5                   10                  15

<210> SEQ ID NO 15

```
<211> LENGTH: 30
<212> TYPE: PRT
<213> ORGANISM: Borreliella burgdorferi

<400> SEQUENCE: 15

Lys Asp Leu Lys Asn Lys Ile Leu Lys Ile Lys Lys Glu Ala Thr Gly
1               5                   10                  15

Lys Gly Val Leu Phe Glu Ala Phe Thr Gly Leu Lys Thr Gly
            20                  25                  30

<210> SEQ ID NO 16
<211> LENGTH: 56
<212> TYPE: PRT
<213> ORGANISM: Artificial
<220> FEATURE:
<223> OTHER INFORMATION: Synthetic

<400> SEQUENCE: 16

Val Gln Glu Gly Val Gln Gln Glu Gly Ala Gln Gln Pro Gly Gly Gly
1               5                   10                  15

Met Thr Leu Phe Leu Phe Ile Ser Cys Asn Asn Ser Gly Lys Asp Gly
            20                  25                  30

Asn Thr Ser Ala Gly Gly Gly Met Lys Lys Asn Asp Gln Ile Val Ala
        35                  40                  45

Ala Ile Ala Leu Arg Gly Val Ala
    50                  55

<210> SEQ ID NO 17
<211> LENGTH: 33
<212> TYPE: PRT
<213> ORGANISM: Artificial
<220> FEATURE:
<223> OTHER INFORMATION: Synthetic

<400> SEQUENCE: 17

Val Gln Glu Gly Val Gln Gln Glu Gly Ala Gln Gln Pro Gly Gly Gly
1               5                   10                  15

Met Lys Lys Asn Asp Gln Ile Val Ala Ile Ala Leu Arg Gly Val
            20                  25                  30

Ala

<210> SEQ ID NO 18
<211> LENGTH: 42
<212> TYPE: PRT
<213> ORGANISM: Artificial
<220> FEATURE:
<223> OTHER INFORMATION: Synthetic

<400> SEQUENCE: 18

Val Gln Glu Gly Val Gln Gln Glu Gly Ala Gln Gln Pro Gly Gly Gly
1               5                   10                  15

Met Lys Lys Asp Asp Gln Ile Ala Ala Ala Met Val Leu Arg Gly Met
            20                  25                  30

Ala Lys Asp Gly Gln Phe Ala Leu Lys Asp
        35                  40

<210> SEQ ID NO 19
<211> LENGTH: 4
<212> TYPE: PRT
<213> ORGANISM: Artificial Sequence
<220> FEATURE:
<223> OTHER INFORMATION: Synthetic
```

<400> SEQUENCE: 19

Gly Gly Gly Gly
1

<210> SEQ ID NO 20
<211> LENGTH: 212
<212> TYPE: PRT
<213> ORGANISM: Borreliella burgdorferi

<400> SEQUENCE: 20

```
Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Glu Ser Asn Ala Val Val Leu Ala Val Lys Glu Val Glu Thr
    50                  55                  60

Leu Leu Ala Ser Ile Asp Glu Val Ala Lys Lys Ala Ile Gly Asn Leu
65                  70                  75                  80

Ile Ala Gln Asn Gly Leu Asn Ala Gly Ala Asn Gln Asn Gly Ser Leu
                85                  90                  95

Leu Ala Gly Ala Tyr Val Ile Ser Thr Leu Ile Ala Glu Lys Leu Asp
            100                 105                 110

Gly Leu Lys Asn Ser Glu Glu Leu Lys Glu Lys Ile Glu Asp Ala Lys
        115                 120                 125

Lys Cys Asn Lys Ala Phe Thr Asp Lys Leu Lys Ser Ser His Ala Glu
    130                 135                 140

Leu Gly Ile Ala Asn Gly Ala Ala Thr Asp Ala Asn Ala Lys Ala Ala
145                 150                 155                 160

Ile Leu Lys Thr Asn Gly Thr Lys Asp Lys Gly Ala Gln Glu Leu Glu
                165                 170                 175

Lys Leu Phe Glu Ser Val Lys Asn Leu Ser Lys Ala Ala Gln Glu Thr
            180                 185                 190

Leu Asn Asn Ser Val Lys Glu Leu Thr Ser Pro Val Val Ala Glu Asn
        195                 200                 205

Pro Lys Lys Pro
    210
```

<210> SEQ ID NO 21
<211> LENGTH: 191
<212> TYPE: PRT
<213> ORGANISM: Borreliella burgdorferi

<400> SEQUENCE: 21

```
Met Ile Lys Cys Asn Asn Lys Thr Phe Asn Asn Leu Leu Lys Leu Thr
1               5                   10                  15

Ile Leu Val Asn Leu Leu Ile Ser Cys Gly Leu Thr Gly Ala Thr Lys
            20                  25                  30

Ile Arg Leu Glu Arg Ser Ala Lys Asp Ile Thr Asp Glu Ile Asp Ala
        35                  40                  45

Ile Lys Lys Asp Ala Ala Leu Lys Gly Val Asn Phe Asp Ala Phe Lys
    50                  55                  60

Asp Lys Lys Thr Gly Ser Gly Val Ser Glu Asn Pro Phe Ile Leu Glu
65                  70                  75                  80

Ala Lys Val Arg Ala Thr Thr Val Ala Glu Lys Phe Val Ile Ala Ile
```

-continued

```
                85                      90                      95
Glu Glu Glu Ala Thr Lys Leu Lys Glu Thr Gly Ser Ser Gly Glu Phe
            100                     105                 110

Ser Ala Met Tyr Asp Leu Met Phe Glu Val Ser Lys Pro Leu Gln Lys
        115                     120                 125

Leu Gly Ile Gln Glu Met Thr Lys Thr Val Ser Asp Ala Ala Glu Glu
        130                     135             140

Asn Pro Pro Thr Thr Ala Gln Gly Val Leu Glu Ile Ala Lys Lys Met
145                     150             155                 160

Arg Glu Lys Leu Gln Arg Val His Thr Lys Asn Tyr Cys Thr Leu Lys
                165             170                 175

Lys Lys Glu Asn Ser Thr Phe Thr Asp Glu Lys Cys Lys Asn Asn
            180                 185                 190
```

IMMUNOASSAY TEST DEVICE WITH TWO FLUID FLOW PATHS FOR DETECTION AND DIFFERENTIATION OF TWO OR MORE ANALYTES

CROSS-REFERENCE TO RELATED APPLICATIONS

This application claims the benefit of U.S. Provisional Application No. 62/210,880, filed Aug. 27, 2015 and of U.S. Provisional Application No. 62/268,455, filed Dec. 16, 2015, and of U.S. Provisional Application No. 62/271,101, filed Dec. 22, 2015, each of which is incorporated herein by reference in its entirety.

REFERENCE TO SEQUENCE LISTING, TABLE OR COMPUTER PROGRAM

A Sequence Listing is being submitted electronically via EFS in the form of a text file, created Aug. 25, 2016, and named "0418960942SequenceListing.txt" (9,251 bytes), the contents of which are incorporated herein by reference in their entirety.

TECHNICAL FIELD

The subject matter described herein relates to lateral flow immunoassays that have two separate fluid flow paths to detect and discriminate two species of interest in a fluid sample.

BACKGROUND

Rapid lateral flow immunoassays test devices have an extensive history of use in both the clinical and the home settings. These devices are used to test for a variety of analytes, such as hormones, proteins, urine or plasma components and the like. These devices generally comprise a lateral flow test strip, such as nitrocellulose or filter paper, a sample application area, test results area and an analyte specific binding reagent that is bound to some kind of detectable label, such as a colored particle, fluorescent or luminescent tag, or an enzyme detection system. The simplicity of such devices is a factor in maintaining their use in the marketplace, and additional tests for detection and differentiation of multiple analytes in a single sample are desired.

BRIEF SUMMARY

The following aspects and embodiments thereof described and illustrated below are meant to be exemplary and illustrative, not limiting in scope.

In one aspect, a device for determining presence or absence of infection due to an infectious agent is provided. The device comprises a sample receiving zone configured to receive a liquid sample from a subject suspected of having an infection due to an infectious agent, the sample receiving zone positioned to distribute the sample along a first fluid flow path to a first label zone and along a second fluid flow path to a second label zone. Each of the first and second label zones comprise, respectively, a first mobilizable, detectable species and a second mobilizable, detectable species, each mobilizable, detectable species able to bind the infectious agent or to antibody against the infectious agent. The device also comprises a first test line in the first fluid flow path positioned downstream of the first label zone, the first test line comprising an immobilized species with binding affinity for the first mobilizable detectable species. The device also comprises a second test line in the second fluid flow path positioned downstream of the second label zone, the second test line comprising an immobilized species with binding affinity for the second mobilizable detectable species. The device also comprises a reference line positioned in the first fluid flow path and comprising an immobilized species with binding affinity for a detectable moiety deposited on the device upstream of the reference line.

In one embodiment, the first fluid flow path and the second fluid flow path are at an angle selected from a straight angle (180°), an obtuse angle and an acute angle.

In another embodiment, the reference line in the first fluid flow path is downstream of the first test line.

In yet another embodiment, the device further comprises an additional reference line in the second fluid flow path. In still another embodiment, the additional reference line is downstream of the second test line.

The device, in other embodiments, is designed such that the first test line comprises a first immobilized species that directly binds antibody against the infectious agent present in the liquid sample and that specifically binds a conjugate comprised of the mobilizable, detectable species in the first label zone and an antibody against the infectious agent in the sample.

In other embodiments, the second test line comprises a second immobilized species that directly binds antibody against the infectious agent present in the liquid sample and that specifically binds a conjugate comprised of the mobilizable, detectable species in the second label zone and an antibody against the infectious agent in the sample.

In some embodiments, the first and second immobilized species are the same.

In one embodiment, the mobilizable, detectable species in the first label zone is an anti-IgM antibody. In another embodiment, the anti-IgM antibody is a nonhuman anti-human IgM antibody.

In another embodiment, the immobilized species in the first test line comprises a plurality of antigens for *B. burgdorferi* with binding affinity for the human IgM antibody against *B. burgdorferi*.

In yet another embodiment, the mobilizable, detectable species second label zone is an anti-IgG antibody. In another embodiment, the anti-IgG antibody is a nonhuman anti-human IgG antibody.

In still another embodiment, the immobilized species in the first test line comprises a plurality of antigens for *B. burgdorferi* with binding affinity for the human IgG antibody against *B. burgdorferi*.

In one embodiment, the mobilizable, detectable species comprises a label detectable optically. Examples include but are not limited to a fluorescent or chemiluminescent marker or a detectable particle, such as a europium bead.

In one embodiment, the sample receiving zone is positioned between the first label zone and the second label zone.

In another embodiment, the substrate comprises a single sample receiving zone that is common to the first label zone and the second label zone.

In one embodiment, the first and second test lines are within a single optical path of an optical detector for inspection by an instrument. The single optical path is, in one embodiment, a path along one axis that intersects the first and second test lines.

In another embodiment, the sample receiving zone dispenses sample to the first label zone and the second label zone in essentially equal amounts and at essentially equal rates.

In another aspect, a device for determining presence of infection due to an infectious agent is provided. The device comprises (i) a sample receiving zone configured to receive a liquid sample from a subject suspected of having an infection due to an infectious agent, the sample receiving zone positioned to distribute the sample along a first fluid flow path to a first label zone and along a second fluid flow path to a second label zone, each of said first and second label zones comprising, respectively, a first mobilizable, detectable species and a second mobilizable, detectable species, each mobilizable, detectable species able to bind separate, distinct antibodies against the infectious agent; (ii) a first test line in the first fluid flow path positioned downstream of the first label zone, the first test line comprising an immobilized species with binding affinity for the first mobilizable detectable species; (iii) a second test line in the second fluid flow path positioned downstream of the second label zone, the second test line comprising an immobilized species with binding affinity for the second mobilizable detectable species; (iv) a reference line positioned in the first fluid flow path and comprising an immobilized species with binding affinity for a detectable moiety deposited on the device upstream of the reference line.

In one embodiment, the first mobilizable, detectable species is a non-human, anti-human IgM antibody or a Lyme antigen. In another embodiment, the second mobilizable, detectable species is a non-human, anti-human IgG antibody or a Lyme antigen.

In another embodiment, the immobilized species on the first test line with binding affinity for the first mobilizable detectable species is a non-human, anti-human IgM antibody or a Lyme antigen.

In still another embodiment, the immobilized species on the second test line with binding affinity for the second mobilizable detectable species is a non-human, anti-human IgG antibody or a Lyme antigen.

In yet another embodiment, the reference line is positioned downstream of the first test line.

In other embodiments, the reference line comprises an immobilized species with binding affinity for a non-human, anti-human IgG antibody or a non-human, anti-human IgM antibody.

In one embodiment, the reference line comprises an immobilized species with binding affinity for a substance not present in the liquid sample.

In another embodiment, two or more separate, distinct antibodies against the infectious agent are present in the liquid sample and are capable of binding the immobilized species on each of the first test line and the second test line and capable of binding one of the mobilizable, detectable species on the first label line or on the second label line.

In another embodiment, the separate, distinct antibodies against the infectious agent are present in the liquid sample and are capable of binding the mobilizable, detectable species on the first label line to form a first conjugate and on the second label line to form a second conjugate, and the immobilized species on the first test line has binding affinity for the first conjugate and the immobilized species on the second test line has binding affinity for the second conjugate.

In one embodiment, the immobilized species on the first test line is a non-human, anti-human IgM antibody. In another embodiment, the immobilized species on the first test line is a non-human, anti-human IgG antibody.

In another aspect, a method for staging infection by a pathogenic *Borrelia* species, such as *Borrelia burgdorferi* (*B. burgdorferi*), is provided. The method comprises depositing a fluid sample from a person suspected of or at risk of having been exposed to the pathogenic *Borrelia* species on a device as described herein; and inspecting (using an instrument) the first test line and the second test line for the presence or absence of the mobilizable detectable species.

In one embodiment, the fluid sample is blood, cerebrospinal fluid or urine.

In another embodiment, the fluid sample is blood and is deposited in an amount of less than 50 µL.

In other embodiment, inspecting is performed in about 10 minutes or less after depositing the fluid sample.

In still other embodiments, depositing and inspecting provides sensitivity to detect an IgM antibody response to *B. burgdorferi* exposure in greater than 70% of exposed subjects within 2 weeks of exposure. In another embodiment, depositing and inspecting provides sensitivity to detect an IgG antibody response to *B. burgdorferi* exposure in greater than 70% of exposed subjects within 2 weeks of exposure.

In addition to the exemplary aspects and embodiments described above, further aspects and embodiments will become apparent by reference to the drawings and by study of the following descriptions.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE SEQUENCES

Figure 1A:
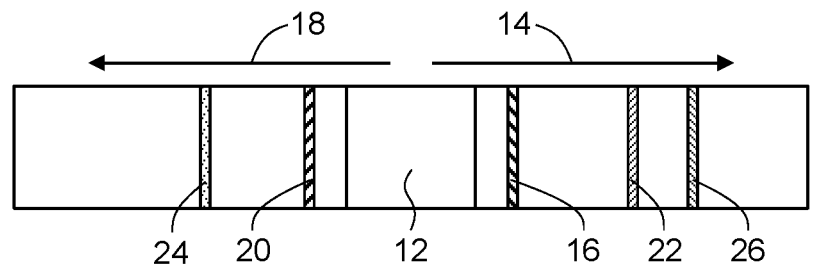
FIGS. 1A-1B are top views of two embodiments of a test device having first and second fluid flow paths.

SEQ ID NO: 1 is a peptide antigen with binding affinity to an epitope from a pathogenic strain of *Borrelia*: MKKNDQIVAAIALRGVA SEQ ID NO: 2 is a peptide antigen with binding affinity to an epitope from a pathogenic strain of *Borrelia*: CMKKDDQIAAAMVLRGMAKDGQFALK SEQ ID NO: 3 is a peptide antigen with binding affinity to an epitope from a pathogenic strain of *Borrelia*: MKKNDQIGAAIALRGVA SEQ ID NO: 4 is a peptide antigen with binding affinity to an epitope from a pathogenic strain of *Borrelia*: MKKDDQIAAAIALRGMA SEQ ID NO: 5 is a peptide antigen with binding affinity to an epitope from a pathogenic strain of *Borrelia*: MKKDDQIAAAMVLRGMAKDGQFALKD SEQ ID NO: 6 is a peptide antigen with binding affinity to an epitope from a pathogenic strain of *Borrelia*: MKKDDQIAAAIALRGMAKDGKFAVKD SEQ ID NO: 7 is a peptide antigen with binding affinity to an epitope from a pathogenic strain of *Borrelia*: VQEGVQQEGAQQP SEQ ID NO: 8 is a peptide antigen with binding affinity to an epitope from a pathogenic strain of *Borrelia*: PVVAESPKKP SEQ ID NO: 9 is a peptide antigen with binding affinity to an epitope from a pathogenic strain of *Borrelia*: CPVVAESPKKP SEQ ID NO: 10 is a peptide antigen with binding affinity to an epitope from a pathogenic strain of *Borrelia*: LCPVVAESPKKP SEQ ID NO: 11 is a peptide antigen with binding affinity to an epitope from a pathogenic strain of *Borrelia*: YGQNWTNPENMVTSGPFKLKERIPNEKIVFEKNNK SEQ ID NO: 12 is a peptide antigen with binding affinity to an epitope from a pathogenic strain of *Borrelia*: MTLFLFISCNNSGKDGNTSA SEQ ID NO: 13 is a peptide antigen with binding affinity to an epitope from a pathogenic strain of *Borrelia*: KMTLFLFISCNNSGKDGNTSA SEQ ID NO: 14 is a peptide antigen with binding affinity to an epitope from a pathogenic strain of *Borrelia*: TILVNLLISCGLTGA SEQ ID NO: 15 is a peptide antigen with binding affinity to an epitope from a pathogenic strain of *Borrelia*: KDLKNKILKIKKEATGKGVLFEAFTGLKTG SEQ ID NO: 16 is a fusion peptide antigen with binding affinity to epitopes from a pathogenic strain of *Borrelia*: VQEGVQQEGAQQPGGGMTLFLFISCNNSGKDGNTSAGGGMKKNDQIVAAIALRGVA SEQ ID NO: 17 is a fusion peptide antigen with binding affinity to epitopes from a pathogenic strain of *Borrelia*: VQEGVQQEGAQQPGGGMKKNDQIVAAIALRGVA SEQ ID NO: 18 is a fusion peptide antigen with binding affinity to epitopes from a pathogenic strain of *Borrelia*: VQEGVQQEGAQQPGGGMKKDDQIAAAMVLRGMAKDGQFALKD SEQ ID NO: 19 is a synthetic linker peptide: GGGG SEQ ID NO: 20 is the amino acid sequence of the outer surface protein C of *Borreliella burgdorferi* (GenBank Acc. No. WP_012686633.1).

SEQ ID NO: 21 is the amino acid sequence of the decorin-binding protein A of *Borreliella burgdorferi* (GenBank Acc. No. WP_010890380.1).

DETAILED DESCRIPTION

I. Definitions

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µM.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

"Sample" is any material to be tested for the presence or amount of an analyte of interest. Preferably, a sample is a fluid sample, preferably a liquid sample. Examples of liquid samples that may be tested using a test device include bodily fluids including blood, serum, plasma, saliva, urine, ocular fluid, semen, sputum, nasal discharge and spinal fluid.

A "test strip" can include one or more bibulous or non-bibulous materials. If a test strip comprises more than one material, the one or more materials are preferably in fluid communication. One material of a test strip may be overlaid on another material of the test strip, such as for example, filter paper overlaid on nitrocellulose. Alternatively or in addition, a test strip may include a region comprising one or more materials followed by a region comprising one or more different materials. In this case, the regions are in fluid communication and may or may not partially overlap one another. Suitable materials for test strips include, but are not limited to, materials derived from cellulose, such as filter paper, chromatographic paper, nitrocellulose, and cellulose acetate, as well as materials made of glass fibers, nylon, dacron, PVC, polyacrylamide, cross-linked dextran, agarose, polyacrylate, ceramic materials, and the like. The material or materials of the test strip may optionally be treated to modify their capillary flow characteristics or the characteristics of the applied sample. For example, the sample application region of the test strip may be treated with buffers to correct the pH or specific gravity of an applied urine sample, to ensure optimal test conditions.

II. Device

In a first aspect, a device for determining presence of infection due to an infectious agent is provided. Various embodiments of the device will be described with reference to certain drawing figures.

A first embodiment of a device is shown in FIG. 1A. A test strip 10 comprises a sample receiving zone 12 configured to receive a liquid sample. Typically, the sample is from a subject suspected of having an infection due to an infectious agent, and examples of types of patient samples and of infectious agents are described below. Sample receiving zone 12 is positioned to distribute the sample along a first fluid flow path, indicated by arrow 14 in FIG. 1A, to a first label zone 16 and along a second fluid flow path, indicated by arrow 18 in FIG. 1A, to a second label zone 20. Each of the first and second label zones comprise, respectively, a first mobilizable, detectable species and a second mobilizable, detectable species, where each mobilizable, detectable species is able to bind to the infectious agent or to antibody against the infectious agent, as will be described.

The first fluid flow path and the second fluid flow path as depicted in FIG. 1A are at a straight angle of 180°. In other embodiments, the first fluid flow path and the second fluid flow path can be at an obtuse angle from one another or at an acute angle from one another.

Test strip 10 also comprises a first test line 22 in the first fluid flow path and positioned downstream of the first label zone (16). The first test line comprises an immobilized species with binding affinity for the first mobilizable detectable species. Binding affinity intends indirect binding or direct binding between two species, such as direct binding of an antigen to an antibody or indirect binding of a secondary antibody to a conjugate formed of a primary antibody and an antigen, where the secondary antibody and primary antibody have binding affinity. For example, in one embodiment, an antibody in the patient sample is indicative of presence of infection by an infectious agent, and the antibody in the patient sample binds a mobilizable, detectable species comprised of a non-human antibody with binding affinity for the antibody in the patient sample or an antigen of or from the infectious agent indicative of the suspected infection.

Test strip 10 also comprises a second test line 24 in the second fluid flow path (18) and positioned downstream of the second label zone (20). The second test line comprises an immobilized species with binding affinity for the second mobilizable, detectable species present in the second label zone. Binding affinity intends indirect binding or direct binding between two species, as described in the preceding paragraph.

Figure 1B:
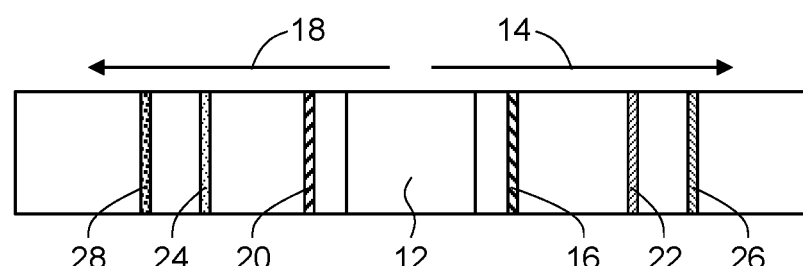

Test strip 10 also comprises a reference line 26 positioned in the first fluid flow path (14) and comprising an immobilized species with binding affinity for a detectable moiety deposited on or formed on the device upstream of the reference line. In one embodiment, reference line 26 is downstream of first test line 22. Optionally, and as depicted in FIG. 1B where like elements are denoted by like numerical identifiers as in FIG. 1A, the test strip comprises a second or additional reference line 28 in the second fluid flow path (18). In one embodiment, the additional reference line is downstream of the second test line 24.

As mentioned above, in one embodiment, the first test line comprises an immobilized species that directly binds an antibody present in the patient sample, the antibody being one raised by the patient's immune system against the infectious agent of interest and suspected of being the cause of infection in the patient. In another embodiment, the first test line comprises an immobilized species that binds a conjugate formed on the test device, the conjugate comprised of (i) the mobilizable, detectable species in the first label zone and (ii) an antibody present in the patient sample, the antibody being one raised by the patient's immune system against the infectious agent of interest and suspected of being the cause of infection in the patient.

The second test line, in various embodiments, comprises an immobilized species that directly binds antibody against the infectious agent, the antibody being one raised by the patient's immune system against the infectious agent of interest and suspected of being the cause of infection in the patient. In another embodiment, the second test line comprises an immobilized species that binds a conjugate formed on the test device, the conjugate comprised of (i) the mobilizable, detectable species in the second label zone and (ii) an antibody present in the patient sample, the antibody being one raised by the patient's immune system against the infectious agent of interest and suspected of being the cause of infection in the patient.

An illustrative test strip with continuing reference to FIGS. 1A-1B is now described. In this exemplary test strip, it is desired to determine whether a subject is at risk of Lyme disease or has Lyme disease, or, alternatively, it is desired to determine if infection with a *Borrelia* species, such as but not limited to *Borrelia burgdorferi, Borrelia afzelii, Borrelia garinii, Borellia japonica*, is at an early stage or a late stage of infection. To achieve these desires, a test strip that comprises a single, individual sample receiving zone is provided, and a patient's sample is deposited on or in the sample receiving zone. The sample receiving zone is common to two fluid flow paths on the test strip, where a first fluid flow path carries a portion of the deposited sample in a first direction and a second fluid flow path carries a second portion of the deposited sample in a second direction. In one embodiment, the two fluid flow paths and their directions of fluid flow are at 180° from each other, so that the paths are along a common axis. Each of the two fluid flow paths comprises a label zone that comprises a mobilizable, detectable species. The mobilizable, detectable species in the exemplary test strip for staging or detecting infection by a species in the *Borrelia* genus is, in a first embodiment, a non-human, anti-human antibody that has or is associated with a detectable label. The non-human, anti-human antibody is, in some embodiments, a non-human, anti-human IgG antibody bearing a detectable label, such as a fluorescent, chemiluminescent, or other optically detectable tag, such as a bead or chemical moiety. The non-human, anti-human antibody is, in some embodiments, a non-human, anti-human IgM antibody bearing a detectable label, such as a fluorescent, chemiluminescent, or other optically detectable tag, such as a bead or chemical moiety. In one embodiment, optically detectable intends optically detectable by an instrument and not visually detectable by an unaided human eye.

In this exemplary test strip, the detectable non-human, anti-human IgM antibody is deposited on the first label line, and the detectable non-human, anti-human IgG antibody is deposited on the second label line. More specifically, a detectable goat anti-human IgM antibody is deposited on the first label line and a detectable goat anti-human IgG antibody is deposited on the second label line. Non-human, anti-human IgG and IgM antibodies are exemplified as goat, anti-human antibodies, however the non-human portion of the antibody can be any mammal, including but not limited to mouse, rabbit, rat, sheep, etc.

Deposited on the first test line of the exemplary test strip for detecting or staging Lyme disease is an antigen for a species in the *Borrelia* genus. For example, for detecting or staging Lyme infection due to *B. burgdorferi*, one or more peptide antigens from *B. burgdorferi* is deposited on the test lines in each of the flow paths on the test strip. In one example, peptide antigens with binding affinity to the OspC, C6, C10, FlaB or BBK07 regions of B. *Burgdorferi* are deposited in an immobile fashion to the test lines. In another embodiment, a recombinant protein with binding affinity to B. *Burgdorferi* or to an antibody against B. *Burgdorferi* is deposited on a test line. For example, the recombinant protein for the outer surface protein C (OspC) of B. *Burgdorferi* (GenBank Acc. No. WP_012686633.1; SEQ ID NO: 20), for the decorin-binding protein A (DbpA) of B. *Burgdorferi* (GenBank Acc. No. WP_010890380.1; SEQ ID NO: 21), or fragments of these proteins that have between 12-60, 12-50, 12-40, 10-40 or 10-25 contiguous amino acid residues from the protein are contemplated, as exemplified by SEQ ID NO: 12 and SEQ ID NO: 14. Other examples of peptide antigens are known in art, such as in U.S. Pat. Nos. 8,338,556; 6,716,574; 6,719,983; 8,071,109; 8,354,240; 6,475,492; 6,660,274; 7,887,815, 5,643,733, and U.S. Patent Publication No. 2015/0017666, which are each incorporated by reference herein.

In one embodiment, the peptide antigen deposited on one or both of the test lines binds the C6 region of *B. burgdorferi* and has a sequence selected from the exemplary sequences set forth as SEQ ID NO: 1, SEQ ID NO: 2, SEQ ID NO: 3, SEQ ID NO: 4, SEQ ID NO: 5 or SEQ ID NO: 6. In other embodiments, the peptide antigen deposited on one or both of the test lines comprises SEQ ID NO: 1, SEQ ID NO: 2, SEQ ID NO: 3, SEQ ID NO: 4, SEQ ID NO: 5 or SEQ ID NO: 6 (or a peptide having 80%, 85%, 86%, 87%, 89%, 90%, 91%, 92%, 93%, 94%, 95%, 96%, 97%, 98%, or 99% sequence identity thereto) and is attached to the test line with a biotin-strepavidin interaction. In one embodiment, the peptide antigens or plurality of peptide antigens deposited on the first test line and on the second test line are the same. In one embodiment, the peptide antigen deposited on one or both of the test lines has 80%, 85%, 86%, 87%, 89%, 90%, 91%, 92%, 93%, 94%, 95%, 96%, 97%, 98%, or 99% sequence identity to one of the peptide or protein sequences disclosed herein.

Figure 2:
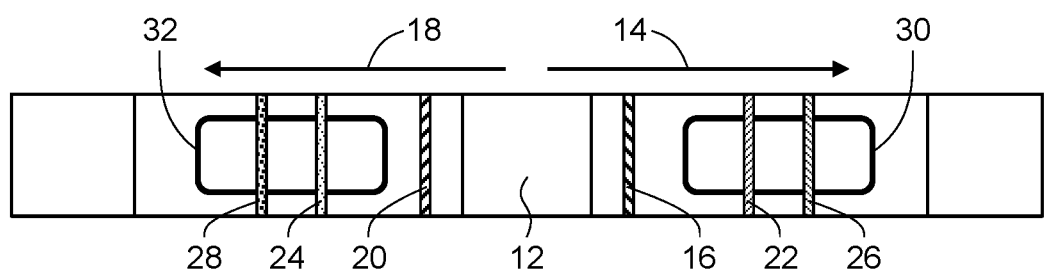
FIG. 2 illustrates a top view of a test device with bilateral fluid flow paths and position of optical windows for inspection of the test and optional reference lines.

The test strips described herein can be used in conjunction with a housing member that encases the test strip. The housing member has one or more apertures, the aperture(s) situated over the sample reservoir and the test lines and the reference line. Materials for housing members are known in the art, as are materials for the test strip itself. FIG. 2 illustrates a top view of a test device where optical windows in the housing member are disposed over the test lines (22, 24) and reference lines (26, 28). Optical window 30 and optical window 32 define an opening visible to a user or an optical reader in an instrument for interrogation of the test and reference lines.

Figure 3:
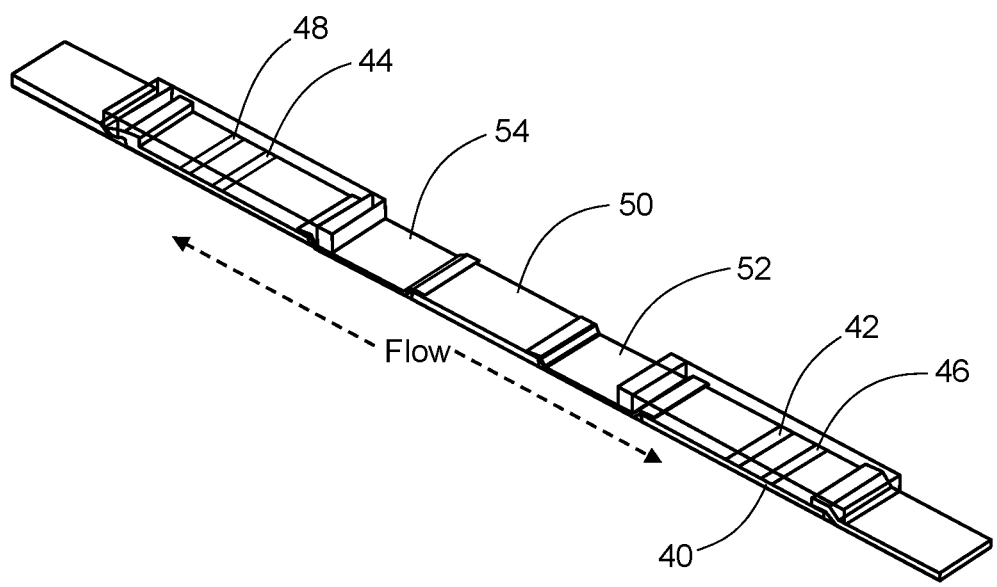
FIG. 3 is a perspective view of a test device with bidirectional fluid flow paths for discrimination of two analytes in a sample.

FIG. 3 is a perspective view of a test device with bidirectional fluid flow paths for discrimination of two analytes in a sample. In this embodiment, the test device has a base nitrocellulose layer 40 on which the test and control lines are deposited, such as test lines 42, 44 and control lines 46, 48. A sample pad 50 is centrally positioned for distribution of sample to each of the test and control lines via a label pad, such as label pads 52, 54. The label pads are of a material suitable for receiving the mobilizable species and situated to overlap with the nitrocellulose layer and the sample pad to provide contiguous fluid communication.

III. Methods of Use

The device described herein is contemplated for use in detection of any pathogenic or infectious agent, and several examples are now described.

A. Detection of Lyme Disease

Lyme disease is transmitted by the bite of various species of *Ixodes* ticks carrying the etiologic agent, a pathogenic *Borrelia* bacterium (a spirochete). Organisms of the *Borrelia burgdorferi* sensu lato group belong to the family Spirochaetaceae, genus *Borrelia*. There are at least 11 species in the *B. burgdorferi* complex and an unknown but large number of substrains. At least three genospecies of the *Borrelia burgdorferi* sensu lato group have been identified as pathogens: *B. burgdorferi* sensu stricto, *B. afzelli*, and *B. garinii*. A current basis for diagnosis in the absence of erythema migrans is the demonstration of an antibody response against a pathogenic *Borrelia*. The test strip described herein provides a sensitive and specific diagnostic method for the detection of Lyme disease, e.g. at early times after infection, and provides a means to stage the infection as early or late stage.

In one embodiment, a test strip with a plurality of peptides immobilized on the first and second test lines in each of the fluid flow paths or mobilizable on the first and second label lines in each of the fluid flow paths is provided. The plurality of peptides can be the same or different in each of the test lines and/or label lines. In one embodiment, the plurality of peptides comprises 3 or more, or 4 or more, or 5 or more, or 6 or more, or 7 or more, or 8 or more, different peptide sequences from a *Borellia* species, such as *B. burgdorferi* sensu lato. In another embodiment, the plurality of peptides comprises more than 2 but 10 or fewer, or more than 2 but 9 or fewer, or more than 2 but 8 or fewer, or more than 2 but 7 or fewer, or more than 2 but 6 or fewer, or more than 2 but 5 or fewer, or more than 2 but 4 or fewer, different peptides that bind specifically to an antibody against a pathogenic *Borellia* species, such as *B. burgdorferi* sensu lato. In one embodiment, the peptides are any combination of peptides with binding to OppA, Bbk32, OspC-typeK, RecA, BmpA, DbpA, ErpP, p35, OspF, CRASP 2, FlilB, p66, OspC-typeA, FlaB, or DdpB. In another embodiment, the plurality of peptide antigens includes a peptide that comprises an epitope from *Borrelia* flagellin p41 (e.g., a peptide having the sequence VQEGVQQEGAQQP (SEQ ID NO: 7)), and/or an epitope from *Borrelia* OspC (e.g., a peptide having the sequence PVVAESPKKP (SEQ ID NO: 8)), including active (i.e., those that specifically bind) variants thereof. Alternatively, or in addition, the plurality of peptide antigens includes a peptide that comprises an epitope from the VLsE (region IR6) *Borrelia* protein (e.g. the 26 amino acid peptide CMKKDDQIAAA MVLRGMAKDGQFALK (SEQ ID NO: 2)), or a shorter peptide from this region, such as a peptide with 12-18 contiguous resides from SEQ ID NO: 2 or 12-18 non-contiguous residues from SEQ ID NO: 2, exemplified by the peptide MKKNDQIGAAIALRGVA (SEQ ID NO: 3), or active variants thereof.

The antigen anchored to the test strip can also be a fusion peptide of one, two, three, four or more peptides that bind to an antibody against a pathogenic *Borrelia* species, such as *B. burgdorferi* sensu lato. A skilled artisan can appreciate the variety of possible combination and the variety of linkers to join the peptides. Examples are provided herein where, for example, a FlaB peptide (p41, SEQ ID NO: 7) is attached by a linker to a C6 peptide (SEQ ID NO: 1, SEQ ID NO: 2, SEQ ID NO: 3, SEQ ID NO: 4, SEQ ID NO: 5 or SEQ ID NO: 6) to form a fusion peptide as exemplified by SEQ ID NO: 16, SEQ ID NO: 17 and SEQ ID NO: 18. Another example is set forth herein as SEQ ID NO: 16 which consists of a peptide from the p41 (FlaB) region (SEQ ID NO: 2) linked to a peptide from the OspC1 region (SEQ ID NO: 12) linked to a peptide for the C6 region (SEQ ID NO: 1), the three peptides joined by a linker comprised of three amino acid residues (GGG). In still other embodiments, the linker peptide comprises 1, 2, 3, 4, 5, 6, 7, 8, 9, 10 or more amino acids. In yet other embodiments, the linker comprises 1 to 2, 1 to 5, 2 to 5, 2 to 4, 1 to 10, 5 to 10, 3 to 6, or 2 to 10 amino acids. In still other embodiments, the linker is G, GG, GGG, or GGGG (SEQ ID NO: 19).

Suitable linkers for joining any of the peptide sequences disclosed herein can be readily selected and can be of any of a suitable of different lengths, such as from 1 amino acid (e.g., Gly) to 40 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids. In some embodiments, the linker comprises only glycines. In other embodiments, 1, 2 3 or 4 of the glycines are substituted with serines.

Non-peptide linker moieties can also be used to join or link a carrier moiety to a mitochondrial fusion modulatory peptide. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

It will be appreciated that the peptides disclosed herein and referenced by incorporation herein are merely exemplary of the peptide sequences that can be used in an assay. Embodiments of the assay contemplate use of peptide sequences that have 80%, 85%, 86%, 87%, 89%, 90%, 91%, 92%, 93%, 94%, 95%, 96%, 97%, 98%, or 99% sequence identity to any of the sequences disclosed herein, when the two sequences are compared along their entire length. It will also be appreciated that any of the sequences may be biotinylated, including biotinylated at the N-terminus, the C-terminus, or at an amine residue in an amino acid within the first one, two, three, four, five amino acids (counting from the N-terminal amino acid) of the peptide. It will also be appreciated that any of the sequence may be modified at the N-terminus, the C-terminus, or both with a reactive moiety or a chemical linking moiety, such as a hydroxyl, carboxyl, amine or group.

Examples 1-4 relate to test strips for detection of IgG and IgM antibodies against a pathogenic *Borrelia* species (Examples 1-3) and for staging as early state or late stage an infection by a pathogenic *Borrelia* species (Example 4). The test strips are designed to detect the presence of immunoglobulins raised by a human subject infected with a pathogenic *Borrelia* species. After infection, IgM antibodies develop over a three to six week period, and this is referred to in the art, and herein, as an early stage infection. IgG antibodies develop within 4-12 weeks after infection, and are indicative of infection at a later stage, and this is referred to herein as late stage infection. Accordingly, an early stage of infection or early stage Lyme disease is indicated by presence of IgM antibodies against a pathogenic *Borrelia* species in a blood sample taken 3-6 weeks after infection, and a late stage of Lyme disease is indicated by presence of IgG antibodies against a pathogenic *Borrelia* species in a blood sample taken 4-12 weeks after infection. In one embodiment, a late state of Lyme disease is additionally indicated by an amount of IgG antibodies in the sample that is greater than the amount of IgM antibodies in the sample. The test strip of Example 1 comprises on the first and second label lines a conjugate of a fluorescent label and a non-human (e.g., goat) antihuman immunoglobulin of IgM or IgG specificity against the pathogenic *Borrelia* species. The blood immunoglobulins in the sample travel along the first and second fluid flow paths to the first and second label lines. At each line, the blood immunoglobulin with specificity for the fluorescent-conjugate goat antihuman immunoglobulin of IgG or IgM binds to the conjugate to form a mobile complex of a specific blood immunoglobulin (IgG or IgM) and a fluorescent conjugate of the antihuman IgG or IgM. The complexes travel downstream to their respective first or second test line, where the blood immunoglobulin portion of the complex binds with the peptide antigens deposited on each of the test lines, thus detecting on one test line blood IgG immunoglobulins for the pathogenic *Borrelia* species and on the other test line blood IgM immunoglobulins for the pathogenic *Borrelia* species.

The test strip of Example 1 is intended to interact with an instrument with an optical reader and software to operate the optical reader, gather signal emitted from the test strip and interpret the gathered signal data. The test strip includes a reference line used by the instrument as a positional control for determination of the position of the first and second test lines. In the test strip embodiment of Example 1, the reference line comprises an immobilized non-human antihuman immunoglobulin specific for IgM (although an immobilized non-human antihuman immunoglobulin specific for IgG could also be used). The immobilized non-human (e.g., rabbit) antihuman IgM antibody binds the mobilizable non-human (e.g., goat) antihuman IgM antibody-detectable conjugate deposited on the label line and binds the complex formed on the label line, the complex of the blood immunoglobulin IgM and the non-human (e.g., goat) antihuman IgM antibody-detectable conjugate. Thus, in this embodiment, the reference line captures the complex comprising the analyte of interest, the blood immunoglobulin raised against the pathogen of interest (in this case, a species of *Borrelia*). For this reason, the reference line is positioned downstream of the test line since if a small amount of the analyte of interest to be detected is present, it would be captured on the reference line and the test strip would return a false negative. A reference line capable of capturing two detectable moieties on the test strip—in this case both the complex formed on the strip and the detectable label species on the label line—increases the detectable signal on the reference line.

An alternative embodiment of a test strip for determining the presence of an immunoglobulin against a pathogenic *Borrelia* species, and thus indicative of the presence or absence of Lyme disease, is described in Example 2. In this test strip, the label line comprises mobilizable, detectable conjugate of one or more peptide antigens with binding specificity to immunoglobulins IgG or IgM in the blood raised against the pathogenic *Borrelia* species and a detectable label. The detectable conjugate binds the blood immunoglobulin, forming a complex that travels downstream to the test line. One test line on the test strip comprises a species with binding affinity to IgG immunoglobulin and the other test line comprises a species with binding affinity to IgM immunoglobulin. In this way, IgG and IgM are discriminated on the test strip at the test lines. In the embodiment of Example 1, IgG and IgM are discriminated on the test strip at the label lines. In the test strip of Example 2, a binding pair that is independent of the antigen-antibody pair associated with the pathogenic *Borrelia* species is used on the reference line. Examples include horse radish peroxidase and anti-horse radish peroxidase and glucose oxidase and anti-glucose oxidase, where one of the binding pair is immobilized on the reference line and the other binding member of the pair is deposited on the test strip upstream of the reference line. Accordingly, test devices with a reference line that comprises an immobilized species with binding affinity for a substance not present in the liquid sample are contemplated.

Another embodiment of a test strip for determining the presence of an immunoglobulin against a pathogenic *Borrelia* species, and thus indicative of the presence or absence of Lyme disease, is described in Example 3. One test line on the test strip comprises a species with binding affinity to IgG immunoglobulin and the other test line comprises a species with binding affinity to IgM immunoglobulin. In this way, IgG and IgM are discriminated on the test strip. On one side of the sample reservoir (e.g., see FIG. 1A) in a downstream to upstream direction are deposited a first label line comprising mobilizable goat anti-human IgM antibodies attached to europium beads. Downstream from this first label line is a first test line with immobilized peptide antigens for the OspC region (e.g., peptide antigens identified as SEQ ID NO: 12 or SEQ ID NO: 13) and the DbpA region (e.g., peptide antigen identified as SEQ ID NO: 14)

of *B. burgdorferi*. A reference line with immobilized rabbit anti-goat IgM antibodies is downstream of the first label line. On the opposing side of the sample reservoir (e.g., see FIG. 1A) in a downstream to upstream direction are deposited a second label line comprising mobilizable mouse anti-human IgG antibodies bound to europium beads and a second test line with immobilized peptide antigens for the C10 (SEQ ID NO: 8 or SEQ ID NO: 10), C6 (SEQ ID NO: 1, SEQ ID NO: 2, SEQ ID NO: 3, SEQ ID NO: 4, SEQ ID NO: 5 or SEQ ID NO: 6) and p41 (FlaB; SEQ ID NO: 7) epitopes of *B. burgdorferi*. The peptide antigens were modified to include a biotin moiety at the N-terminus or in the N-terminal region and anchored to the test strip via binding with an anchored streptavidin molecule.

It can also be appreciated from the exemplary test strips that herein provide a means to differentiate separate, distinct antibodies raised against the same infectious agent. The test strips comprise an immobilized species on each of the first test line and the second test line that bind each of the separate, distinct antibodies raised against the same infectious agent, and discriminate the two separate, distinct antibodies by the use of a mobilizable, detectable species specific for one of the separate, distinct antibodies on the first label line and on the second label line.

As mentioned above, the tests strip of Example 1-3 can be used to stage as early stage or late stage an infection by a pathogenic *Borrelia* species. As described in Example 4, the method comprises depositing a fluid sample from a person suspected of or at risk of having been exposed to the pathogenic *Borrelia* species on a device as described herein, and inspecting the first test line and the second test line for the presence or absence of the mobilizable detectable species. In one embodiment, depositing and inspecting provides sensitivity to detect an IgM antibody response to *B. burgdorferi* exposure in greater than 70% of exposed subjects within 2 weeks of exposure. In another embodiment, depositing and inspecting provides sensitivity to detect an IgG antibody response to *B. burgdorferi* exposure in greater than 70% of exposed subjects within 2 weeks of exposure.

In another study, detailed in Example 5, a test strip as depicted in FIG. 1A was prepared by positioning a common, single sample pad centrally on a strip of nitrocellulose. To one side of the single, common sample pad in a downstream to upstream direction was deposited a plurality of detectable markers (e.g., europium beads) with surface bound goat anti-human IgM antibodies to form a first label line. Downstream of the first label line a first test line was deposited, the first test line composed of recombinant OspC (SEQ ID NO: 20) and recombinant DbpA (SEQ ID NO: 21), each linked at its N-terminus to biotin and immobilized to the nitrocellulose via streptavidin. Downstream of the first test line was deposited a rabbit anti-goat IgG antibody to form a reference line on the nitrocellulose. On the opposing side of the common, single sample pad, in a downstream to upstream direction, was deposited a plurality of detectable markers (e.g., europium beads) with surface bound mouse anti-human IgG antibodies to form a second label line. Downstream of the second label line a second test line was deposited, the second test line composed immobilized peptide antigens for the C10 (SEQ ID NO: 8), C6 (SEQ ID NO: 6) and C6-p41 (SEQ ID NO: 18) epitopes of *B. burgdorferi*. The peptide antigens were modified to include a biotin moiety at the N-terminus or in the N-terminal region and anchored to the nitrocellulose substrate via binding with an anchored streptavidin molecule. The C10 peptide antigen was modified at its C-terminus with a hydroxyl group. An absorbent pad was positioned on each end of the test strip.

Blood samples from individuals presenting with acute erythema migrans (an early stage indication of Lyme disease) or with Lyme arthritis (an indicator of late stage Lyme disease) were obtained, as well as blood samples from healthy individuals to serve as a negative control. The samples were diluted with buffer and a known volume was placed on the sample pad of the test strip. Each test strip was incubated and then inserted into an instrument with an optical system and software to interrogate the test lines and the reference lines for presence or absence of the detectable markers.

The results from the instrument-read test strips were interpreted and compared to results from enzyme immunoassay (EIA), Western Blot, and the two-tiered testing for Lyme disease recommended by the Center for Disease Control and Prevention. Of the eight (8) early Lyme erythema migrans samples, both the instrument-read test strips for IgM detection and the Western Blot IgM detected ⅝ (62.5%), and the samples tested by EIA for IgM detected 4/8 (50%), suggesting that the instrument-read test strip is more sensitive than EIA for early stage Lyme detection. Accordingly, in one embodiment, a test strip as described herein provides a sensitivity for detection of IgM that is greater than that provided by enzyme immunoassay, for detection of Lyme disease or for staging Lyme disease as early stage or late stage.

Of the four (4) late Lyme samples tested, the instrument-read test strips for IgG, Western Blot IgG and EIA detected all of the samples (100%) suggesting that the instrument-read test strip for IgG has sensitivity equivalent to detection of IgG via Western Blot and EIA. Accordingly, in one embodiment, a test strip as described herein provides a sensitivity for detection of IgG that is essentially the same as that provided by Western blot and/or by enzyme immunoassay, for detection of Lyme disease or for staging Lyme disease as early stage or late stage.

With regard to the control samples, the instrument-read test strip of IgM and IgG and Western Blot IgM and IgG were negative for all twenty (20) negative control samples tested (100% negative agreement). The EIA reported four (4) samples positive (80% negative agreement). This demonstrates that the instrument-read test strip for IgM and IgG is more specific than EIA and equivalent to IgM and IgG Western Blot. Accordingly, in one embodiment, a test strip as described herein provides a specificity for detection of IgM and/or IgG that is greater or higher than that provided by enzyme immunoassay, for detection of Lyme disease or for staging Lyme disease as early stage or late stage.

B. Other Exemplary Test Strips for Detection and Discrimination of Two or More Species In addition to the test strip described above for detection and differentiation of IgG and IgM immunoglobulins against a pathogenic *Borrelia* species, test devices that detect and differentiate or discriminate herpes simplex virus-1 and herpes simplex virus-2 (HSV-1 and HSV-2), influenza A and influenza B (Flu A and Flu B), influenza A+B and respiratory syncytial virus (RSV) are contemplated. Also contemplated is a test strip for detection and differentiation of IgA and IgG associate with Zika virus. As can be appreciated, the bidirectional test strip with two separate fluid flow paths communicating from a common sample reservoir provide an approach to differentiating the two or more analytes of interest from a sample placed on the common sample reservoir.

With regard to a test device for detection and differentiation of HSV-1 and HSV-2, a test strip is contemplated that is comprised of a first label line and a second label line each comprising a mobilizable, detectable anti-human IgG antibody. The first test line on the test strip comprises an immobilized antigen with binding affinity for HSV-1 and the second test line on the test strip comprises an immobilized antigen with binding affinity for HSV-2. The reference line is downstream of the first test line and comprises a binding member of a binding pair independent from the HSV infectious pathogen or comprises a non-human antibody that binds the mobilizable, detectable anti-human IgG antibody deposited on the label lines.

With regard to a test device for detection and differentiation of Flu A and Flu B, a test strip is contemplated that is comprised of a first label line with a mobilizable, detectable anti-flu A nucleoprotein antibody and a second label line with a mobilizable, detectable anti-flu B nucleoprotein antibody. The first test line and the second test lines, respectively, comprise an immobilized anti-flu A nucleoprotein antibody and an immobilized anti-flu B nucleoprotein antibody. The reference line is downstream of the first test line and comprises a binding member of a binding pair independent from the Flu A, Flu B infectious pathogen or comprises a non-human antibody that binds the mobilizable, detectable anti-flu A (or flu B) nucleoprotein antibody deposited on the label line.

With regard to a test device for detection and differentiation of Flu A/B and RSV, a test strip is contemplated that is comprised of a first label line with a mobilizable, detectable anti-flu A/B nucleoprotein antibody and a second label line with a mobilizable, detectable anti-RSV antibody. The first test line and the second test lines, respectively, comprise an immobilized anti-flu A/B nucleoprotein antibody and an immobilized anti-RSV antibody. The reference line is downstream of the first test line and comprises a binding member of a binding pair independent from the infectious pathogens or interest or comprises a non-human antibody that binds the mobilizable, detectable antibody deposited on a label line.

Accordingly, the device herein is designed to determine presence of infection due to an infectious agent, and is able to detect and discriminate two analytes (or two or more analytes) in a biological sample that are indicative of the infectious agent. The device comprises a sample receiving zone configured to receive a liquid sample from a subject suspected of having an infection due to an infectious agent, the sample receiving zone positioned to distribute the sample along a first fluid flow path to a first label zone and along a second fluid flow path to a second label zone. Each of the first and second label zones comprise, respectively, a first mobilizable, detectable species and a second mobilizable, detectable species, each mobilizable, detectable species able to bind separate, distinct antibodies against the infectious agent. The device also comprises a first test line in the first fluid flow path positioned downstream of the first label zone, the first test line comprising an immobilized species with binding affinity for the first mobilizable detectable species. The device also comprises a second test line in the second fluid flow path positioned downstream of the second label zone, the second test line comprising an immobilized species with binding affinity for the second mobilizable detectable species. The device also comprises a reference line positioned in the first fluid flow path and comprising an immobilized species with binding affinity for a detectable moiety deposited on the device upstream of the reference line.

In one embodiment, the volume of fluid sample deposited on the device is less than about 100 μL, preferably less than 75 μL, preferably less than 50 μL, preferably between 10-75 μL, preferably between 10-60 μL and preferably between 10-50 μL.

In another embodiment, the test yields a detectable signal at the first and/or second test line within about 20 minutes or less after depositing the fluid sample, or within about 15 minutes or less after depositing the fluid sample, or within about 10 minutes or less after depositing the fluid sample, or between about 10-30 minutes after depositing the fluid sample, or between about 10-45 minutes after depositing the fluid sample.

IV. Examples

The following examples are illustrative in nature and are in no way intended to be limiting.

Example 1

Test Strip for Detecting Presence of Antibodies Against *B. burgdorferi*

A lateral flow immunoassay device for detection of the presence or absence of IgG and IgM antibodies in the blood of a human is prepared as follows. A test strip is constructed to have a centrally-positioned sample pad that serves as a common sample reservoir for the test strip. On one side of the sample reservoir (e.g., see FIG. 1A) in a downstream to upstream direction are deposited a first label line comprising goat anti-human IgM antibodies attached to a europium bead, a first test line with immobilized peptide antigens comprised of the peptide sequences listed below, and a reference line with immobilized rabbit anti-goat IgM antibodies. On the opposing side of the sample reservoir (e.g., see FIG. 1A) in a downstream to upstream direction are deposited a second label line comprising goat anti-human IgG antibodies bound to a europium bead and a second test line with immobilized peptide antigens comprised of the peptide sequences listed below. The peptide antigens immobilized through a streptavidin moiety attached to the test strip and a biotin attached to each peptide and deposited in each of the first and second test lines are:

```
                                         (SEQ ID NO: 4)
MKKDDQIAAAIALRGMA (SEQ ID NO: 11)
YGQNWTNPENMVTSGPFKLKERIPNEKIVFEKNNK (SEQ ID NO: 12)
MTLFLFISCNNSGKDGNTSA;
and (SEQ ID NO: 16)
VQEGVQQEGAQQPGGGMTLFLFISCNNSGKDGNTSAGGGMKKNDQIVAAI
ALRGVA
```

An absorbent pad is positioned on each end of the test strip.

A blood sample from a human suspected of having Lyme disease caused by *B. burgdorferi* is deposited on the sample reservoir. 15 minutes later, the test strip is inserted into an instrument with an optical system and software to determine presence or absence of europium in the first test line and in the second test line. The instrument uses signal from the reference line to determine position of the first and second test lines.

Example 2

Test Strip for Detecting Presence of Antibodies Against *B. burgdorferi*

A lateral flow immunoassay device for detection of the presence or absence of IgG and IgM antibodies in the blood of a human is prepared as follows. A test strip is constructed to have a centrally-positioned sample pad that serves as a common sample reservoir for the test strip. On one side of the sample reservoir (e.g., see FIG. 1A) in a downstream to upstream direction are deposited a first label line comprising a plurality of peptide antigens from *B. burgdorferi*, each having specific binding to antibodies against *B. burgdorferi* and attached to a europium bead; a first test line with immobilized goat-anti-human IgG antibodies; and a reference line with immobilized anti-glucose oxidase antibodies. The first label line comprises glucose oxidase enzyme attached to a europium bead that travels downstream with the fluid sample. On the opposing side of the sample reservoir (e.g., see FIG. 1A) in a downstream to upstream direction are deposited a second label line comprising a plurality of peptide antigens from *B. burgdorferi*, each having specific binding to antibodies against *B. burgdorferi* and attached to a europium bead; and a second test line with immobilized goat-anti-human IgM antibodies. The peptide antigens deposited on the first and second label lines are:

```
                                       (SEQ ID NO: 4)
MKKDDQIAAAIALRGMA (SEQ ID NO: 11)
YGQNWTNPENMVTSGPFKLKERIPNEKIVFEKNNK (SEQ ID NO: 12)
MTLFLFISCNNSGKDGNTSA;
and (SEQ ID NO: 16)
VQEGVQQEGAQQPGGGMTLFLFISCNNSGKDGNTSAGGGMKKNDQIVAAI
ALRGVA
```

An absorbent pad is positioned on each end of the test strip.

A blood sample from a human suspected of having Lyme disease caused by *B. burgdorferi* is deposited on the sample reservoir. 15 minutes later, the test strip is inserted into an instrument with an optical system and software to determine presence or absence of europium in the first test line and in the second test line. The instrument uses signal from the reference line to determine position of the first and second test lines.

Example 3

Test Strip for Detecting Presence of Antibodies Against *B. burgdorferi*

A lateral flow immunoassay device for detection of the presence or absence of IgG and IgM antibodies in the blood of a human is prepared as follows. A test strip is constructed to have a centrally-positioned sample pad that serves as a common sample reservoir for the test strip. On one side of the sample reservoir (e.g., see FIG. 1A) in a downstream to upstream direction are deposited a first label line comprising mobilizable goat anti-human IgM antibodies attached to europium beads, a first test line with immobilized peptide antigens for the OspC region (SEQ ID NO: 12) and the DbpA region (SEQ ID NO: 14) of *B. burgdorferi*, and a reference line with immobilized rabbit anti-goat IgM antibodies. On the opposing side of the sample reservoir (e.g., see FIG. 1A) in a downstream to upstream direction are deposited a second label line comprising mobilizable mouse anti-human IgG antibodies bound to europium beads and a second test line with immobilized peptide antigens for the C10 (SEQ ID NO: 8 or SEQ ID NO: 10), C6 (SEQ ID NO: 1, SEQ ID NO: 2, SEQ ID NO: 3, SEQ ID NO: 4, SEQ ID NO: 5 or SEQ ID NO: 6) and p41 (FlaB; SEQ ID NO: 7) epitopes of *B. burgdorferi*. The peptide antigens were modified to include a biotin moiety at the N-terminus or in the N-terminal region and anchored to the test strip via binding with an anchored streptavidin molecule.

An absorbent pad is positioned on each end of the test strip.

A blood sample from a human suspected of having Lyme disease caused by *B. burgdorferi* is deposited on the sample reservoir. 15 minutes later, the test strip is inserted into an instrument with an optical system and software to determine presence or absence of europium in the first test line and in the second test line. The instrument uses signal from the reference line to determine position of the first and second test lines.

Example 4

Test Strip for Staging Infection by *B. burgdorferi*

A test strip as described in Example 1 is prepared. A blood sample is taken from a female subject presenting with symptoms of myalgia, fatigue and erythema migrans. The blood sample is deposited on the sample pad of the test strip. 20 minutes later, the test strip is inserted into an instrument with an optical system and software to determine quantity or relative quantities of IgG and IgM antibodies against B. *Burgdorferi* in the blood sample. The test line where IgM antibodies against B. *Burgdorferi* in the blood sample are captured emits a detectable signal when probed by the instrument. The test line where IgG antibodies against B. *Burgdorferi* in the blood sample are captured emits a detectable signal when probed by the instrument. The signal emitted at the test line of IgG antibodies is greater than the signal emitted at the test line of IgM antibodies, indicative of a later stage infection as IgG antibodies are raised 4-12 weeks after infection (E. D. Shapiro and P. Auwaerter, INFECTIOUS DISEASE AND ANTIMICROBIAL AGENTS: *Borrelia burgdorferi* (Lyme Disease), 2002 Edition).

Example 5

Test Strip for Detecting Antibodies Against *B. burgdorferi*

A test strip was prepared as follows. A sample pad was centrally positioned on a strip of nitrocellulose. To one side of the single, common sample pad (e.g., see FIG. 1A) in a downstream to upstream direction was deposited a plurality of europium beads with surface bound goat anti-human IgM antibodies to form a first label line. Downstream of the first label line a first test line was deposited, the first test line composed of recombinant OspC (SEQ ID NO: 20) and recombinant DbpA (SEQ ID NO: 21), each linked at its N-terminus to biotin and immobilized to the nitrocellulose via streptavidin. Downstream of the first test line was deposited a rabbit anti-goat IgG antibody to form a reference line on the nitrocellulose. On the opposing side of the sample pad, in a downstream to upstream direction, was deposited a plurality of europium beads with surface bound mouse anti-human IgG antibodies to form a second label line. Downstream of the second label line a second test line was deposited, the second test line composed immobilized peptide antigens for the C10 (SEQ ID NO: 8), C6 (SEQ ID NO: 6) and C6-p41 (SEQ ID NO: 18) epitopes of *B. burgdorferi*. The peptide antigens were modified to include a biotin moiety at the N-terminus or in the N-terminal region and anchored to the nitrocellulose substrate via binding with an anchored streptavidin molecule. The C10 peptide antigen was modified at its C-terminus with a hydroxyl group. An absorbent pad was positioned on each end of the test strip.

Blood samples from individuals presenting with acute erythema migrans (an early stage indication of Lyme disease) or with Lyme arthritis (an indicator of late stage Lyme disease) were obtained, as well as blood samples from healthy individuals to serve as a negative control. Using a calibrated micropipette, blood samples were diluted 1:10 in a buffer (i.e., blood sample volume of 25 µL in 250 µL buffer). Using a calibrated micropipette, 100 µl of the diluted blood sample was added to the sample port of a test device for contact with the sample pad. Each test strip was incubated for 10 minutes and then inserted into an instrument with an optical system and software to interrogate the test lines and the reference lines for presence or absence of the detectable europium bead. The results from each test device run were interpreted as either positive (above the assay cutoff) or negative (below the assay cutoff).

The results from the instrument read test strips were interpreted and compared to results from enzyme immunoassay (EIA), Western Blot, and the two-tiered testing for Lyme disease recommended by the Center for Disease Control and Prevention. Of the eight (8) early Lyme erythema migrans samples, both the instrument-read test strips for IgM detection and the Western Blot IgM detected 5/8 (62.5%), and the samples tested by EIA for IgM detected 4/8 (50%), suggesting that the instrument-read test strip is more sensitive than EIA for early stage Lyme detection. Accordingly, in one embodiment, a test strip as described herein provides a sensitivity for detection of IgM that is greater than that provided by enzyme immunoassay, for detection of Lyme disease or for staging Lyme disease as early stage or late stage.

Of the four (4) late Lyme samples tested, the instrument-read test strips for IgG, Western Blot IgG and EIA detected all of the samples (100%) suggesting that the instrument-read test strip for IgG has sensitivity equivalent to detection of IgG via Western Blot and EIA. Accordingly, in one embodiment, a test strip as described herein provides a sensitivity for detection of IgG that is essentially the same as that provided by Western blot and/or by enzyme immunoassay, for detection of Lyme disease or for staging Lyme disease as early stage or late stage.

With regard to the control samples, the instrument-read test strip of IgM and IgG and Western Blot IgM and IgG were negative for all twenty (20) negative control samples tested (100% negative agreement). The EIA reported four (4) samples positive (80% negative agreement). This demonstrates that the instrument-read test strip for IgM and IgG is more specific than EIA and equivalent to IgM and IgG Western Blot. Accordingly, in one embodiment, a test strip as described herein provides a specificity for detection of IgM and/or IgG that is greater or higher than that provided by enzyme immunoassay, for detection of Lyme disease or for staging Lyme disease as early stage or late stage.

There was 100% agreement between the instrument-read test strip for IgM and Western Blot IgM results across the positive and negative samples. There was 90.6% agreement between the instrument-read test strip for IgG and Western Blot IgG results. There was a 96.8% agreement between the instrument-read test strip (IgM+IgG) results with the 2-Tier method.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A device, comprising:

only one sample receiving zone, the sample receiving zone configured to receive a liquid sample from a subject suspected of comprising an analyte of interest, the sample receiving zone positioned to distribute the sample along a first fluid flow path to a first label zone and along a second fluid flow path, distinct from the first fluid flow path, to a second label zone, each of said first and second label zones comprising, respectively, a first mobilizable, detectable species that binds IgM antibodies specific to the analyte of interest present in the liquid sample and a second mobilizable, detectable species that binds IgG antibodies specific to the analyte of interest present in the liquid sample; and only one reference line, wherein the reference line is positioned in the first fluid flow path and comprises an immobilized species with binding affinity for a detectable moiety deposited on the device upstream of the reference line;

wherein the device comprises a first test line in the first fluid flow path positioned downstream of the first label zone, the first test line comprising a first immobilized species that is capable of directly binding the IgM antibodies and that is capable of specifically binding a conjugate comprised of the first mobilizable, detectable species and the IgM antibodies, and wherein the first immobilized species comprises an antigen from the analyte of interest; and wherein the device comprises a second test line in the second fluid flow path positioned downstream of the second label zone, the second test line comprising a second immobilized species that is capable of directly binding the IgG antibodies and that is capable of specifically binding a conjugate comprised of the second mobilizable, detectable species and the IgG antibodies, and wherein the second immobilized species comprises an antigen from the analyte of interest.

2. The device of claim 1, wherein the first fluid flow path and the second fluid flow path are at an angle selected from a straight angle (180°), an obtuse angle and an acute angle.

3. The device of claim 1, wherein the reference line is downstream of the first test line.

4. The device of claim 1, wherein the mobilizable, detectable species in the first label zone comprises a nonhuman anti-human IgM antibody.

5. The device of claim 4, wherein the immobilized species in the first test line comprises a plurality of antigens for *B. burgdorferi* with binding affinity for the human IgM antibody against *B. burgdorferi*.

6. The device of claim 1, wherein the mobilizable, detectable species second label zone comprises a nonhuman anti-human IgG antibody.

7. The device of claim 6, wherein the immobilized species in the second test line comprises a plurality of antigens for *B. burgdorferi* with binding affinity for the human IgG antibody against *B. burgdorferi*.

8. The device of claim 1, wherein the mobilizable, detectable species comprises a label detectable optically.

9. The device of claim 8, wherein the optically detectable label is a fluorescent or chemiluminescent marker.

10. The device of claim 1, wherein the sample receiving zone is positioned between the first label zone and the second label zone.

11. The device of claim 1, further comprising a substrate, wherein the sample receiving zone, the first and second fluid flow paths, the first and second label zones, the first and second test lines, and the reference line are deposited on the substrate for direct contact therewith.

12. The device of claim 1, wherein the first and second test lines are within a single optical window for inspection by an instrument.

13. The device of claim 1, wherein the sample receiving zone dispenses sample to the first label zone and the second label zone in essentially equal amounts or at essentially equal rates.

14. A device, comprising:

only one sample receiving zone, the sample receiving zone configured to receive a liquid sample from a subject suspected of comprising an analyte of interest, the sample receiving zone positioned to distribute the sample along a first fluid flow path to a first label zone and along a second fluid flow path, distinct from the first fluid flow path, to a second label zone, the first label zone comprises a mobilizable, detectable nonhuman anti-human IgM antibody that binds IgM antibodies specific to the analyte of interest present in the liquid sample, the second label zone comprises a mobilizable, detectable nonhuman anti-human IgG antibody that binds IgG antibodies specific to the analyte of interest present in the liquid sample; and only one reference line, wherein the reference line is positioned in the first fluid flow path and comprises an immobilized species with binding affinity for a detectable moiety deposited on the device upstream of the reference line;

wherein the device comprises a first test line in the first fluid flow path positioned downstream of the first label zone, the first test line comprising a first immobilized species that is capable of specifically binding a conjugate comprised of the first mobilizable, detectable species and the IgM antibodies specific to the analyte of interest, and wherein the first immobilized species comprises an antigen from the analyte of interest; and wherein the device comprises a second test line in the second fluid flow path positioned downstream of the second label zone, the second test line comprising a second immobilized species that is capable of specifically binding a conjugate comprised of the second mobilizable, detectable species and the IgG antibodies specific to the analyte of interest, and wherein the second immobilized species comprises an antigen from the analyte of interest.

* * * * *

UNITED STATES PATENT AND TRADEMARK OFFICE
CERTIFICATE OF CORRECTION

| | | |
|---|---|---|
| PATENT NO. | : 11,131,670 B2 | Page 1 of 1 |
| APPLICATION NO. | : 15/247633 | |
| DATED | : September 28, 2021 | |
| INVENTOR(S) | : Reed et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1022 days.

Signed and Sealed this
Tenth Day of January, 2023

Katherine Kelly Vidal
*Director of the United States Patent and Trademark Office*